United States Patent [19]

Marciel

[11] Patent Number: Plant 6,031

[45] Date of Patent: Oct. 6, 1987

[54] ROSE PLANT NAMED DE VINE

[75] Inventor: Stanley G. Marciel, Pleasanton, Calif.

[73] Assignee: DeVor Nurseries, Inc., Pleasanton, Calif.

[21] Appl. No.: 787,754

[22] Filed: Oct. 15, 1985

[51] Int. Cl.[4] ..... A01H 5/00
[52] U.S. Cl. ..... Plt./18
[58] Field of Search ..... Plt. 18

*Primary Examiner*—James R. Feyrer

*Attorney, Agent, or Firm*—Chas. W. Rummler; John B. Lungmus

[57] ABSTRACT

A new bright pink hybrid tea rose distinguished by its continuous and profuse year around production of large, bright pink flowers borne on sturdy, upright peduncles carried on main stems or canes having a length of about 90 cm.; by its vigorous, free branching growth habit on strong, upright canes; and by the long lasting character of the bloom both on the plant and as cut flowers.

3 Drawing Figures

BACKGROUND OF THE INVENTION

My new rose plant resulted from a selected seedling produced by me at Pleasanton, Calif., by crossing the pale carmine pink rose variety "Carinella" (U.S. Plant Pat. No. 3,104) with pollen from a stock variety from my collection of rose plants maintained for breeding purposes at Pleasanton with the object of producing a brighter pink flower having an improved production, with longer stems, and on a plant having a vigorous, upright and free branching growth habit. Reproduction of this selected seedling by budding, through successive generations, at Pleasanton, has demonstrated that my aforesaid objectives have been accomplished and that the novel characteristics of the new plant hold true from generation to generation and appear to be firmly fixed.

DESCRIPTION OF THE DRAWING

This new rose plant is illustrated by the accompanying photographic drawings of which sheet one shows a face view in full color of a newly opened flower; and sheet two, in its upper view, shows several stages of flower development from bud to fully opened bloom and in its lower view, shows upper and bottom sides of typical leaves, together with young and old stems with foliage and pieces of the cane; the color rendition of sheet one being as nearly true as it is reasonably possible to obtain by conventional procedures.

DESCRIPTION OF THE NEW VARIETY

The following is a detailed description of my new rose plant based upon observation of plants grown at Pleasanton, Calif., the color designations being according to The R.H.S. Colour Chart published by The Royal Horticultural Society of London, England.

THE PLANT

Origin: Seedling.
Parentage:
- *Seed parent.*—"Carinella" (U.S. Plant Pat. No. 3,104).
- *Pollen parent.*—Seedling No. G64022-39.

Classification:
- *Botanic.*—Hybrid Tea.
- *Commercial.*—Greenhouse Rose.

Form: Upright, compact bush.

Growth rate: Vigorously active.
Height: 182 to 190 cm. to pea size flower.
Cane length: About 90 cm. from hook and generally in proportion to size of bloom.
Growth habit: Free branching, vigorous and upright.
Color: RHS 138A.
Foliage:
- *Quantity.*—Abundant.
- *Number of leaves.*—About 13 to 15 from hook on the flower stem.
- *Leaf shape.*—Odd pinnate.
- *Leaf size.*—About 7 cm. to about 8.3 cm. long.
- *Rachis.*—About 8.2 cm. long for seven leaflet leaf and about 6.2 cm. long on a three leaflet leaf.
- *Petioles.*—Length: About 1.7 cm. from stipule to first blade and from stem to first blade 0.4 cm.

Leaflets: 3 to 7 in number.
- *Size.*—From about 2.8 to 6.2 cm.
- *Shape.*—Oval.
- *Margin.*—Serrate.
- *Texture.*—Moderate leathery.
- *Aspect.*—Smooth and glossy.
- *Color.*—Upper side — Green, RHS 137A. Under side —Green, RHS 138B.
- *Ribs and veins.*—The rib is prominent on both sides of leaflets. The veins are small and almost flat.
- *Stipules.*—Hairy, adnate about 1.8 cm. long and 10.6 cm. wide at widest area.
- *Petiolule.*—About 0.03 cm.

Thorns: The plant has thorns but no splines or prickles.
- *Color.*—Thorns on new wood, Greyed Yellow, RHS 161A.
- *Size.*—About 0.08 cm. long and 0.09 cm. wide at base.

THE BUD

Form: Classical hybrid tea, long, urn-shaped and pointed.
Size: Medium, about 2.8 cm. in diameter and about 4.8 cm. long.
Rate of opening: Very slow.
Color of petals:
- *When sepals first divide.*—Red, RHS 39D, to Red Purple, RHS 62A.
- *When petals begin to unfurl.*—Red Purple, RHS 62A.

Sepals:

*Number.*—Five.
*Shape.*—Ovate acuminate.
*Character.*—Sepals stand up when flower opens and begin to curl back when flower is about three-quarters open.
*Color.*—Inside — Red Purple, RHS 62A. Outside —Red Purple, RHS 62B.

Calyx:
*Shape.*—Funnel shaped.
*Size.*—Large, about 1.3 cm. wide and about 1 cm. long.
*Splitting.*—The calyx does not split.
*Aspect.*—Smooth.

Peduncle: About 12 to 13 cm. long.
*Character.*—Rigid, erect and strong, with very fine hairs.

THE FLOWER

Blooming habit: Profusely and continuous the year around, blooming freely in fall and winter under glass.

Size: Very large.
*Diameter.*—About 10.5 cm.
*Depth.*—About 4.7 cm.

Borne: Singly.

Form: When bloom first opens, high center from ovoid shaped bud. When bloom matures, petals reflex from a swirled imbrication.

Petalage:
*Number.*—About 23 to 30.
*Arrangement.*—Imbricated.
*Form.*—Generally round with entire margins and abrupt points at apex.
*Texture.*—Moderate leathery.
*Aspect.*—Satiny and velvety.
*Color.*—Outer petals, Red Purple, RHS 62A, with Yellow, RHS 4C, at base. Reverse side, overall RHS 62A, with Yellow, RHS 4C, at base. Inside petals, Red Purple, RHS 62A, with Yellow, RHS 4C, at base.

Petaloids:
*Number.*—1 to 3.
*Size.*—About 2.2 cm. long.
*Color.*—Red Purple, RHS 62A, with Yellow, RHS 4C, at base.

Flower stem: About 12 to 13 cm. long.
*Character.*—Upright and sturdy.
*Color.*—Green, RHS 143A.

Persistence: The flower hangs on.

Disease resistance: Moderately resistant to mildew, rust and black spot, as observed in the Bay area of California.

Fragrance: Moderate.

Lasting quality: Long lasting, both on the plant and as a cut flower.

REPRODUCTIVE ORGANS

Stamens:
*Number.*—About 110 to 130 in slightly introrse arrangement.

Anthers:
*Size.*—About 2 mm. long.
*Color.*—Red, RHS 62B.

Filaments:
*Length.*—About 6 to 12 mm.
*Color.*—Yellow, RHS 4D.

Pollen:
*Color.*—Yellow Orange, RHS 21A.

Pistils:
*Number.*—About 95 to 115.

Styles:
*Length.*—About 5 to 7 mm.
*Color.*—Yellow Green, RHS 154D.

Stigmas:
*Color.*—Red, RHS 48D.

Characteristics of ovaries: Ovaries are covered with silvery hairs of Yellow Green, RHS 154D, in color, the styles being unattached to each other throughout. The calyx tube is ovid.

THE FRUIT

Fertility: The fruit is very fertile.

Shape: Pear-shaped.

Color at maturity: Orange, RHS 28B.

This new rose variety most resembles "Carinella" (U.S. Plant Pat. No. 3,104) but is a brighter pink with nicer imbrication and is free blooming with better production, longer stems, and with longer lasting quality in vase.

I claim:

1. A new and distinct variety of rose plant, substantially as herein shown and described, characterized by its profuse and continuous production of rhodamine pink, flowers of generally large size with vigorous, upright, free branching and rapid growth rate habit.

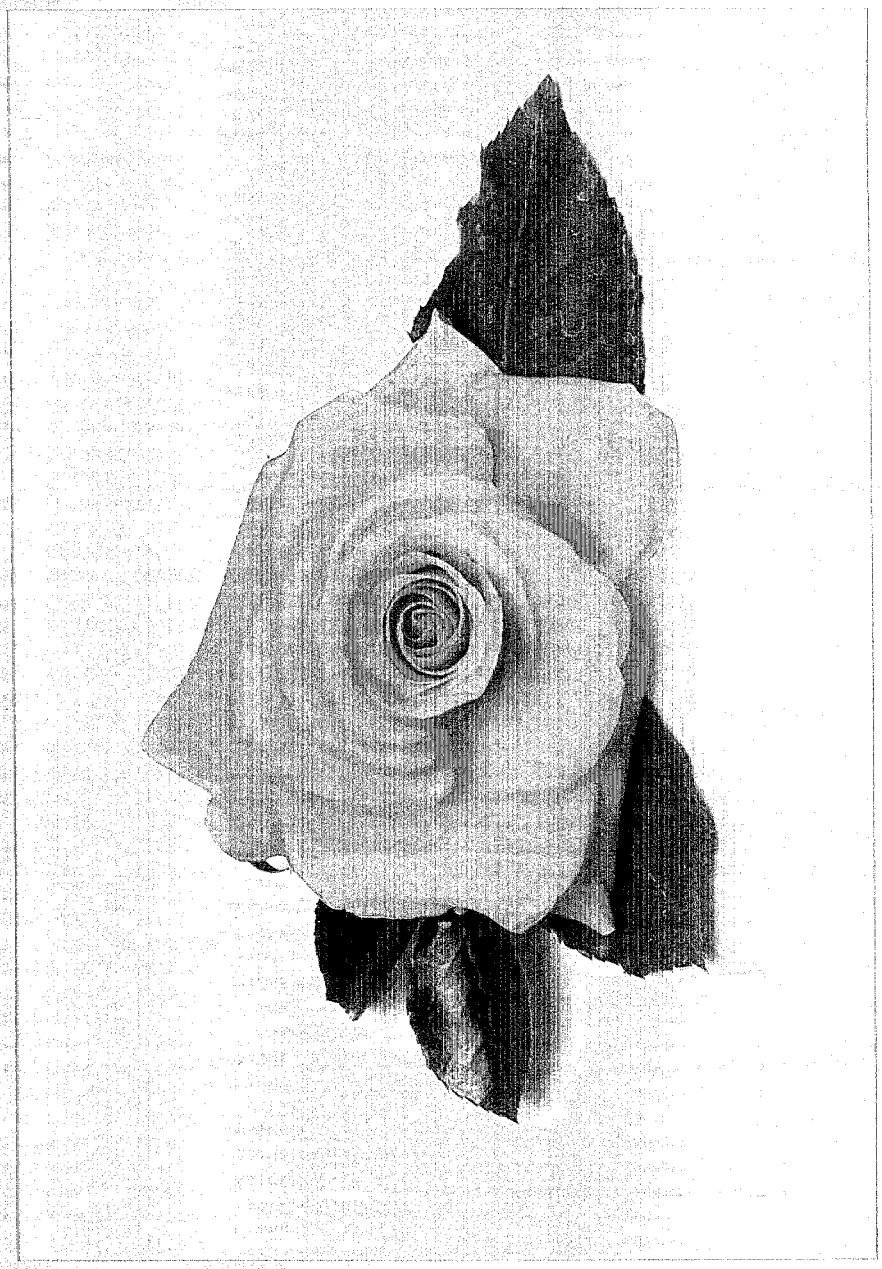

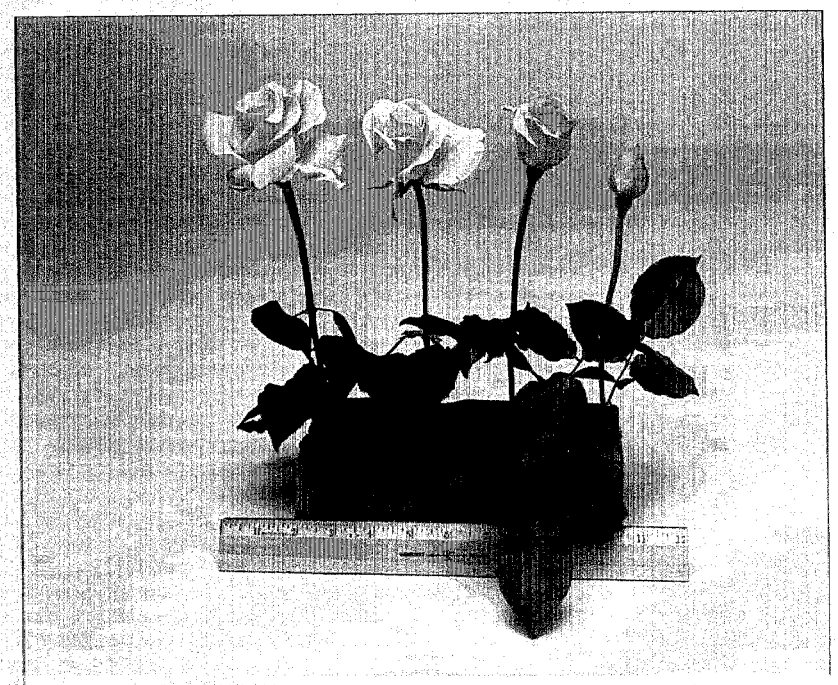
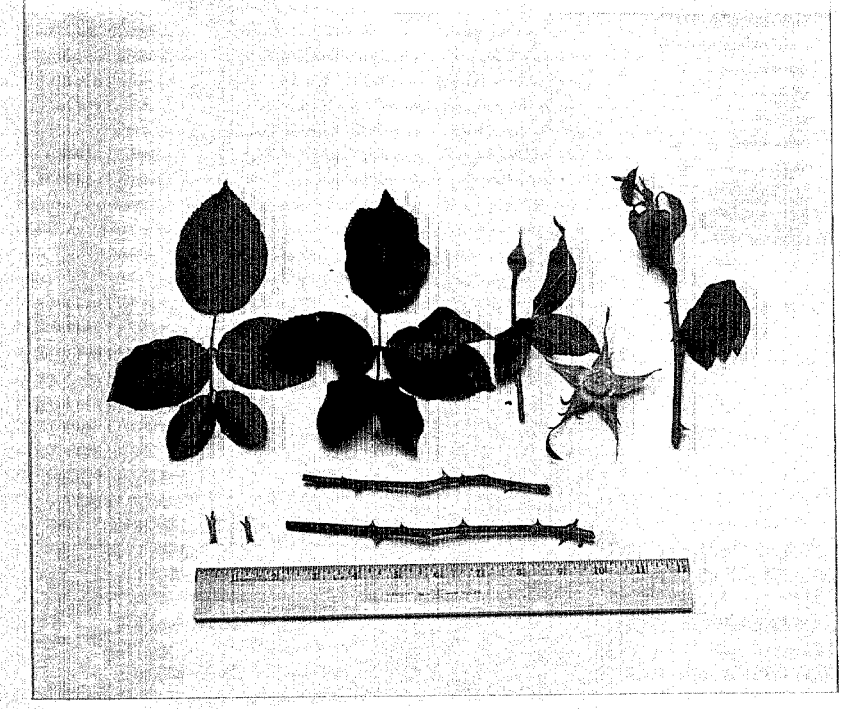

* * * * *